US00PP33870P3

(12) United States Plant Patent
Boches

(10) Patent No.: US PP33,870 P3
(45) Date of Patent: Jan. 18, 2022

(54) BLUEBERRY PLANT NAMED 'FC12-205'

(50) Latin Name: *Vaccinium corymbosum*
Varietal Denomination: FC12-205

(71) Applicant: Fall Creek Farm and Nursery Inc., Lowell, OR (US)

(72) Inventor: Peter Stefan Boches, Hilo, HI (US)

(73) Assignee: FALL CREEK FARM AND NURSERY INC., Lowell, OR (US)

( * ) Notice: Subject to any disclaimer, the term of this patent is extended or adjusted under 35 U.S.C. 154(b) by 0 days.

(21) Appl. No.: 17/166,567

(22) Filed: Feb. 3, 2021

(65) Prior Publication Data

US 2021/0251116 P1 Aug. 12, 2021

Related U.S. Application Data

(60) Provisional application No. 62/995,600, filed on Feb. 6, 2020.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

The new blueberry plant variety 'FC12-205' is provided. 'FC12-205' is a commercial variety intended for the fresh fruit market. The variety is produced from a cross of 'ZF06-103' (female parent, unpatented) and 'ZF06-264' (male parent, unpatented), which can be distinguished by its outstanding features, including late-season ripening, large, uniform fruit size and light blue appearance, yellow-green stem color, and flowers with strong floral scent.

6 Drawing Sheets

Latin name of the genus and species:
Genus—*Vaccinium.*
Species—*corymbosum.*
Variety denomination: The new blueberry plant claimed is of the variety denominated 'FC12-205'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L.) plant, referred to as 'FC12-205', as herein described and illustrated. The new blueberry plant variety 'FC12-205' is a commercial variety intended for the fresh fruit market. The variety has high plant vigor, upright growth habit, ripens late-season, and produces large, uniform size fruit. 'FC12-205' was selected for its above average fruit quality compared to other late-season varieties. The fruit has excellent wax retention resulting in a light blue color, and a lower percentage of shriveled and cracked fruit compared to other varieties in the same harvest window.

'FC12-205' differs from the female parent in that is has a larger, more uniform, fruit size than its female parent 'ZF06-103'. 'FC12-205' differs from the male parent in that it has larger and firmer fruit than 'ZF06-264'.

Pedigree and History: The new blueberry plant originated from a cross of 'ZF06-103' (female parent, unpatented) and 'ZF06-264' (male parent, unpatented) made in Lowell, Oreg., USA in 2008.

The new blueberry variety 'FC12-205' was initially crossed in 2008 in Lowell, Oreg., USA and planted in 2009 in a seedling plot. 'FC12-205' has been found to undergo asexual propagation in Lowell, Oreg. by a number of routes, such as in vitro propagation. Asexual propagation techniques in Lowell, Oreg., such as in vitro propagation, have shown that the characteristics of the new variety are homogenous, stable, and strictly transmissible by such asexual propagation from one generation to another. Accordingly, the new variety undergoes asexual propagation in a true-to-type manner.

'FC12-205' was selected because of its high yield potential, late harvest season, resistance to pre-harvest fruit shrivel and cracking, uniform large fruit size, attractive fruit appearance, and extended cold storage performance.

SUMMARY OF THE INVENTION

The new blueberry plant variety 'FC12-205' has not been observed under all possible environmental conditions. The phenotype may vary somewhat with variations in environment and cultural practices such as temperature and light intensity without, however, any variance in genotype.

'FC12-205' is distinguished by its late ripening season, large uniform fruit size and light blue appearance, bright yellow-green stem color, and pungent smell of the flowers. The following characteristics of the new cultivar have been repeatedly observed and are determined to be the unique characteristics of the new blueberry plant variety 'FC12-205':

1) Late-season ripening
2) Large, uniform fruit size and light blue appearance

3) Yellow-green stem color
4) Flowers with strong floral scent

BRIEF DESCRIPTION OF THE DRAWINGS

The accompanying photographic illustration shows typical specimens in full color of the foliage and fruit of the new variety 'FC12-205'. The colors are as nearly true as is reasonably possible in a color representation of this type.

Figure 1:
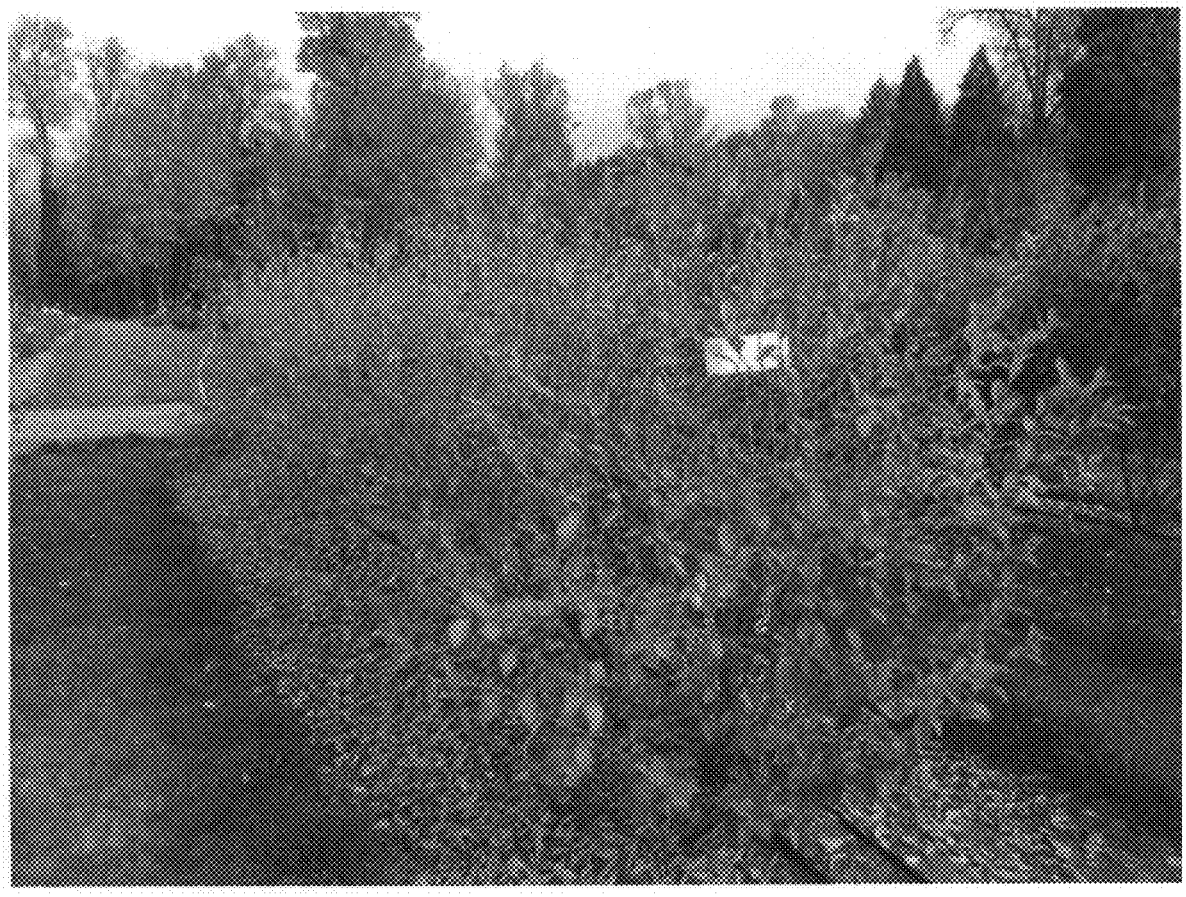
FIG. 1 is a photograph of the new variety 'FC12-205', demonstrating the plant's leaves and growth habit in the fall. The plants were grown in Lowell, Oreg. and photographed on Nov. 16, 2018.
Figure 2:
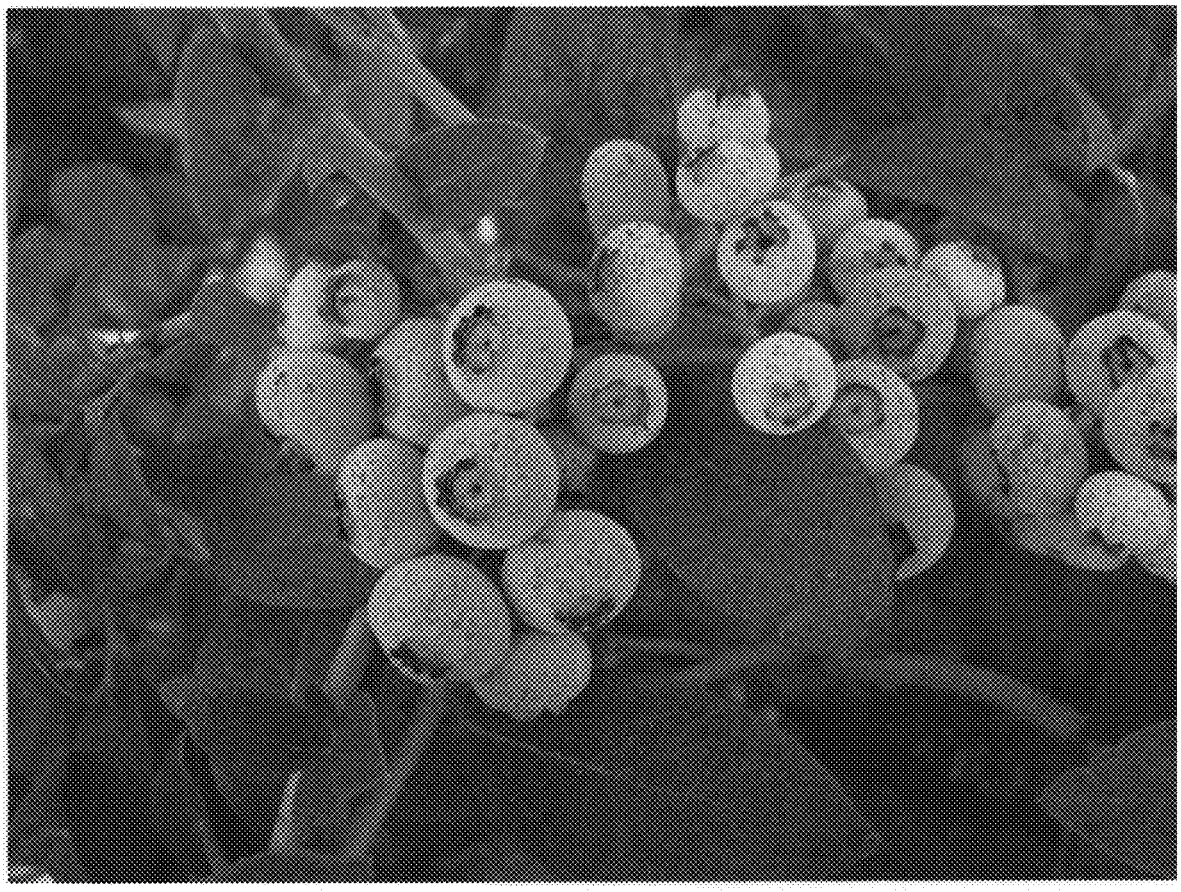
FIG. 2 is a photograph of the fruit cluster of the new variety 'FC12-205' grown in Lowell, Oreg. and photographed on Aug. 1, 2017.
Figure 3:
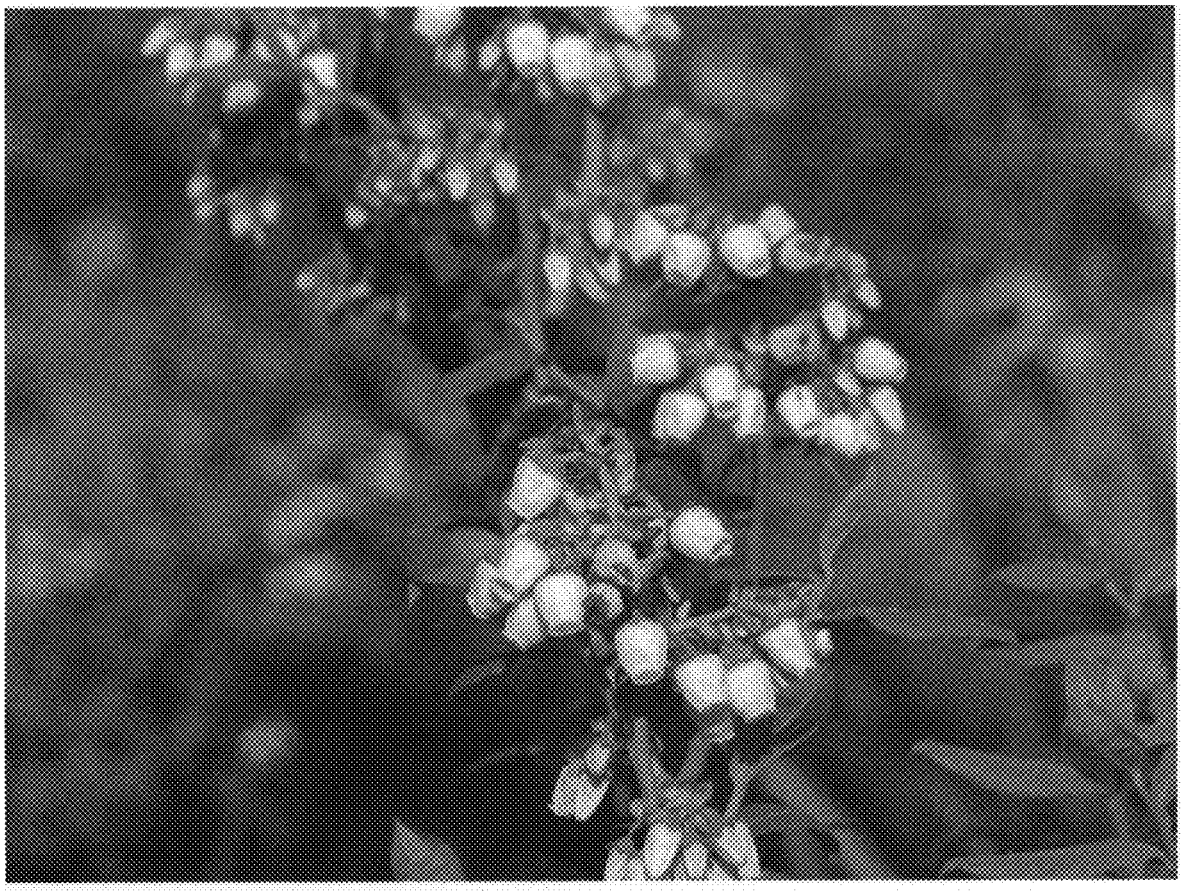
FIG. 3 is a photograph of the flowers of the new variety 'FTC12-205' grown in Lowell, Oreg. and photographed on May 4, 2017.
Figure 4:
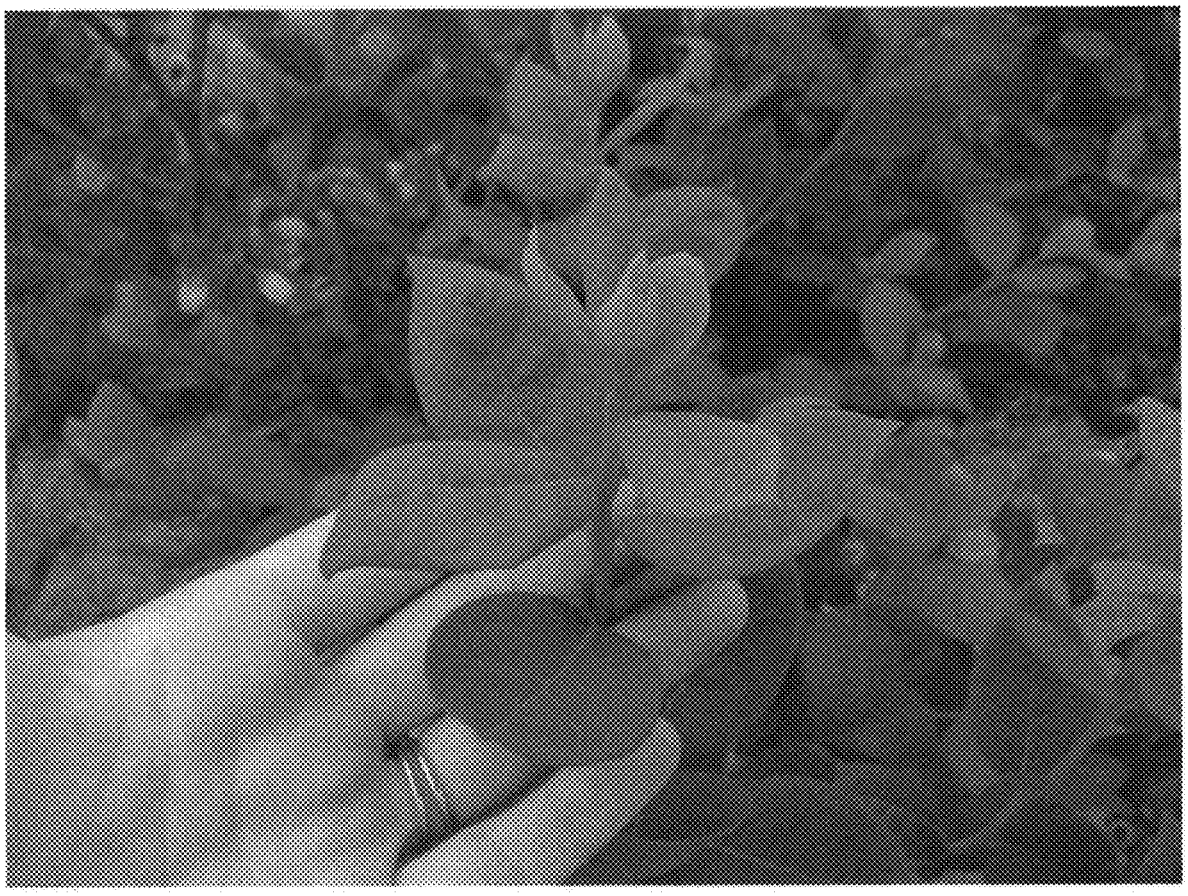
FIG. 4 is a photograph of the spring foliage of the new variety 'FC12-205' grown in Lowell, Oreg. and photographed on May 30, 2017.
Figure 5:
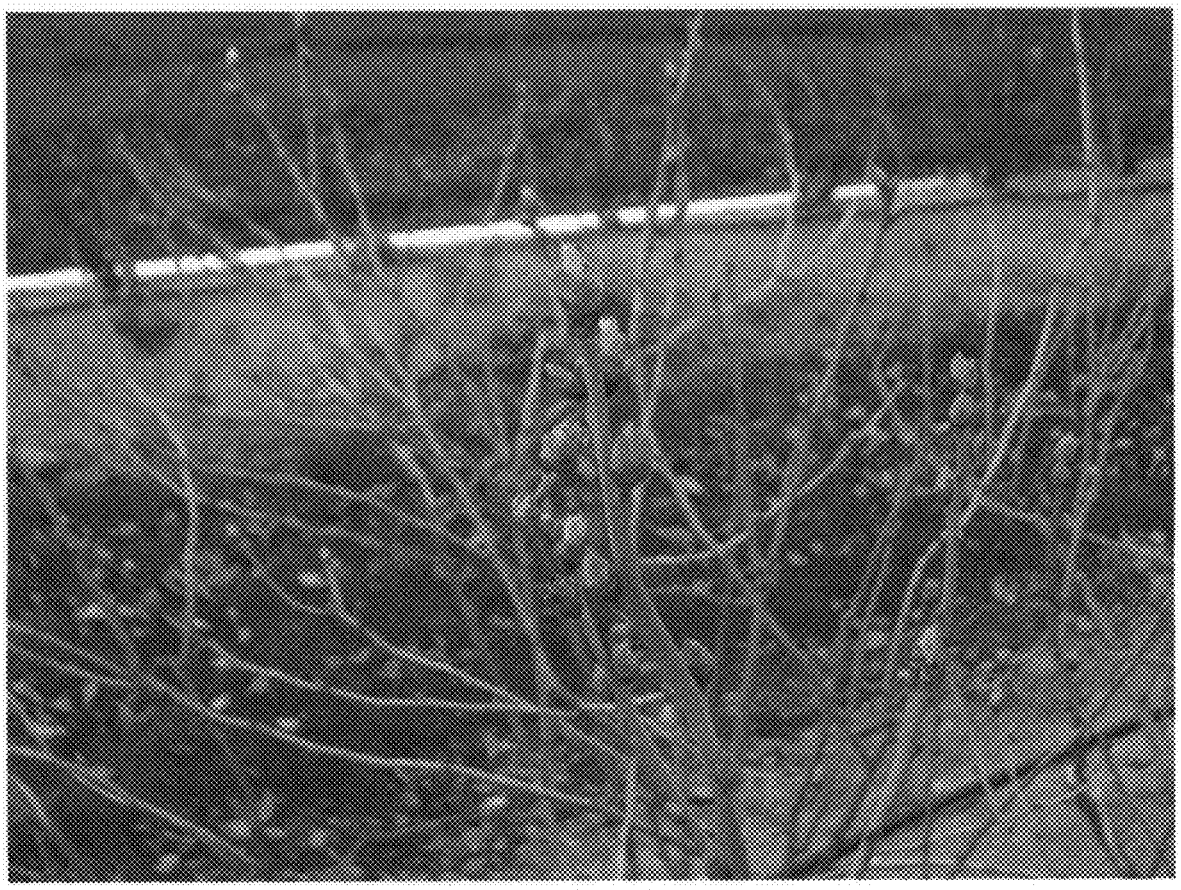
FIG. 5 is a photograph of early buds on the new variety 'FC12-205' grown in Lowell, Oreg. and photographed on Mar. 16, 2017.
Figure 6:
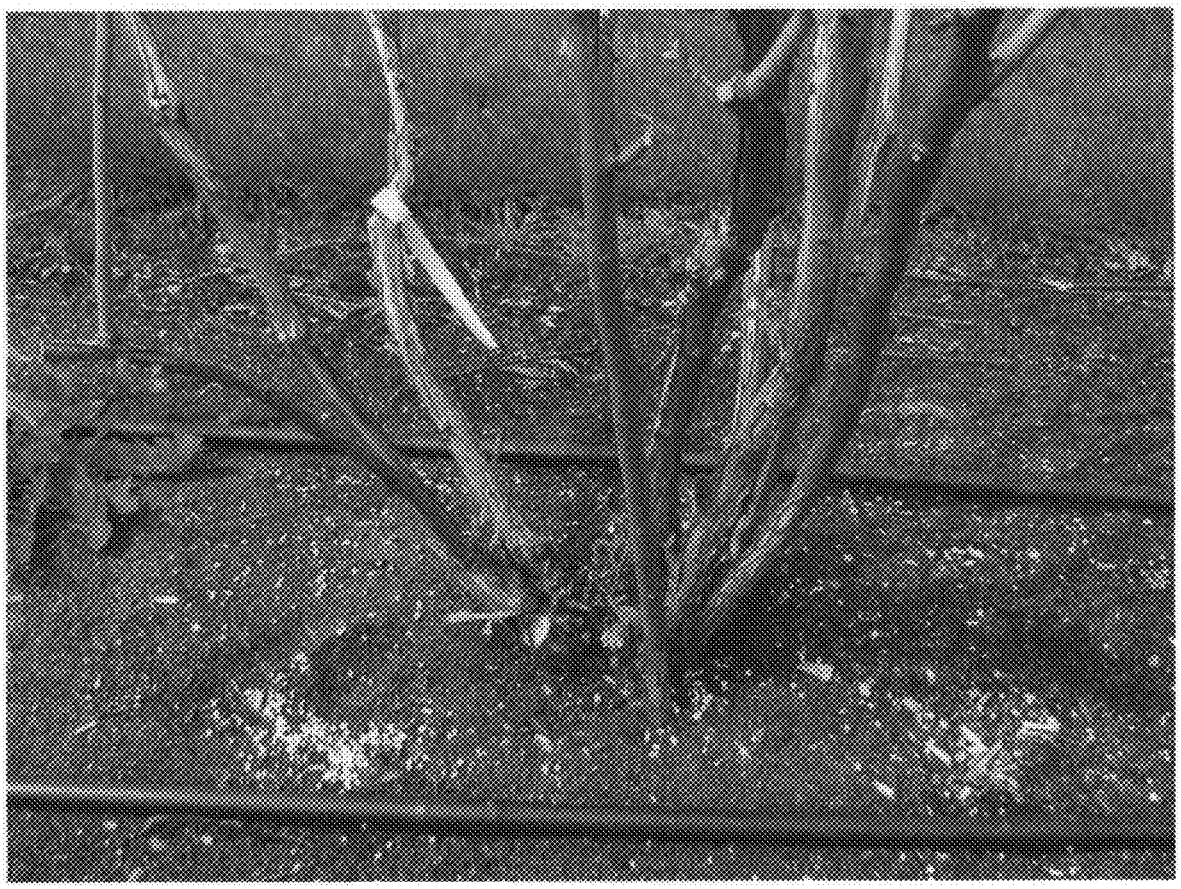
FIG. 6 is a photograph of one-year old canes on the new variety 'FC12-205' grown in Lowell, Oreg. and photographed on Apr. 18, 2018.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FC12-205'. The data which defines these characteristics was collected from asexual reproductions of the original selection. Dimensions, sizes, colors, and other characteristics are approximations and averages set forth as accurately as possible. The plant history was taken on plants approximately 6 years of age, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

Classification:

a. *Family*.—Ericaceae.
b. *Genus*.—*Vaccinium*.
c. *Species*.—*Corymbosum*.
d. *Common name*.—Northern Highbush Blueberry.

Parentage: Female Parent — 'ZF06-103' (unpatented). Male Parent — 'ZF06-264' (unpatented).

Market class: Commercial production of fresh fruit, but suitable for process market.

PLANT

General:

a. *Parentage*.—Female Parent —'ZF06-103' (unpatented). Male Parent — 'ZF06-264' (unpatented).
b. *Plant height*.—Average 162.56 cm.
c. *Plant width*.—Average 203.20 cm.
d. *Growth habit*.—Upright.
e. *Amount of growth in a season* (*i.e., plant vigor*).—High.
f. *Productivity*.—High, three-years old plants typically yield 6.9 lbs per plant.
g. *Cold hardiness*.—Good. In Central and Northwest Washington, there has been no cold damage.
h. *Chilling requirement*.—Estimated minimum of 800-1000.
i. *Leafing*.—Good.
j. *Twigginess*.—Moderately twiggy.
k. *Resistance/susceptibility to root rot* (*phytopthora cinnamomii*).—Not overly susceptible.
l. *Resistance/susceptibility to stem blight* (*botryosphaeria sp.*).—Not overly susceptible.
m. *Resistance/susceptibility to phomopsis twig blight* (*phomopsis vaccinii*).—Not overly susceptible.
n. *Resistance/susceptibility to botrytis* (*botrytis cinerea*).—Not overly susceptible.
o. *Resistance/susceptibility to leaf spot* (*septoria spp.*).—Not overly susceptible.
p. *Resistance/susceptibility to leaf rust* (*naohidemyces vaccinii*).—Not overly susceptible.
q. *Resistance/susceptibility to bud mites* (*acalatus vaccinii*).—Not overly susceptible.

STEM

General:

a. *Suckering tendency*.—Low.
b. *Mature cane color*.—Pantone color 17-1417 (Beaver fur).
c. *Mature cane length*.—152.4 cm.
d. *Mature cane width*.—Average 15.63 mm.
e. *Bark texture*.—Rough.
f. *Fall color on new shoots*.—Pantone color 18-550 (Aurora Red).
g. *Surface texture of new wood*.—Smooth.
h. *Internode length on strong, new shoots*.—19.62 mm.
i. *Average number of buds per fruiting lateral*.—Average 6.

FOLIAGE

General:

a. *Time of beginning of leaf bud burst*.—In Lowell, Oreg., mid-April.
b. *Leaf color* (*top side*).—Pantone color 19-0315 (Black Forest).
c. *Leaf color* (*under side*).—Pantone color 15-6414 (Reseda).
d. *Leaf arrangement*.—Alternate and Spirally Arranged.
e. *Leaf shape*.—Elliptic.
f. *Leaf margins*.—Entire.
g. *Undulation of margin*.—entire.
h. *Leaf venation*.—Anastomosing.
i. *Leaf apices*.—Acute to attenuate.
j. *Leaf bases*.—Obtuse.
k. *Leaf length*.—Average 60.78 mm.
l. *Leaf width*.—Average 32.79 mm.
m. *Leaf length/width ratio*.—1.85.
n. *Leaf nectarines*.—Absent.
o. *Pubescence of upper side*.—Absent.
p. *Pubescence of lower side*.—Absent.

q. *Cross sectional profile*.—Flat.
r. *Longitudinal profile*.—Plane.
s. *Attitude*.—Porrect.
t. *Fall foliage leaf color* (*top side*).—Pantone color 17-1558 (Grenadine).

Petioles:
a. *Length*.—3.887 mm.
b. *Width*.—1.712 mm.
c. *Color*.—Pantone color 14-0434 (Green Banana).
d. *Petiole surface texture*.—Smooth.

FLOWERS

General:
a. *Time of beginning of flowering*.—Approximately mid to late April in Lowell, Oreg.
b. *Time of* 50% *anthesis*.—Approximately early May in Lowell, Oreg.
c. *Flower shape*.—Urceolate.
d. *Flower bud density*.—Medium.
e. *Flower fragrance*.—Pungent, sweet, floral.
f. *Immature flower color*.—Pantone color 11-0602 (Snow White).
g. *Self-compatibility*.—Very good, 93% of self-pollinated flowers produced fruit.

Corolla:
a. *Color*.—Pantone color 11-0602 (Snow White).
b. *Length*.—8.214 mm.
c. *Width*.—8.228 mm.
d. *Aperture width*.—3.868 mm.
e. *Anthocyanin coloration of corolla*.—Weak to absent.
f. *Corolla ridges*.—Present.
g. *Protrusion of stigma*.—0.114 mm below the corolla.

Inflorescence:
a. *Length*.—30.436 mm.
b. *Diameter*.—32.78 mm.
c. *Length of peduncle*.—20.954 mm.
d. *Surface texture of peduncle*.—Puberulent.
e. *Color of peduncle*.—Pantone color 17-1633 (Holly Berry).
f. *Length of pedicel*.—8.16 mm.
g. *Surface texture of pedicel*.—Puberulent.
h. *Color of pedicel*.—Pantone color 17-1633 (Holly Berry).
i. *Number of flowers per cluster*.—10.20.
j. *Flower cluster density*.—Large size and medium-tight.

Calyx (with sepals):
a. *Diameter*.—8.542 mm.
b. *Color* (*sepals*).—Pantone color 13-0215 (Reed).

Stamen:
a. *Length*.—6.698 mm.
b. *Number per flower*.—11 stamen per flower.
c. *Filament color*.—Pantone color 13-0442 (Green Glow).

Pistil:
a. *Length*.—10.22 mm.
b. *Ovary color* (*exterior*).—Pantone color 17-0235 (Piquant Green).
c. *Style length*.—8.452 mm.

Anther:
a. *Length*.—4.47 mm.
b. *Number*.—2 per filament.
c. *Color*.—Pantone color 16-1150 (Topaz).

Pollen:
a. *Abundance*.—Moderate.
b. *Color*.—Pantone color 12-0817 (Cornhusk).

FRUIT

General:
a. *Time of fruit ripening*.—Late. The first harvest begins after 'Cargo' (U.S. Plant Pat. No. 24,661) and before 'Last Call' (U.S. Plant Pat. No. 25,386), typically the first week of August in Lowell, Oreg.
b. *Time of* 50% *maturity*.—Approximately the beginning of August in Lowell, Oreg.
c. *Fruit development period*.—Averaging 85 days in Lowell, Oreg.
d. *Mean harvest date*.—Averaging August 3$^{rd}$
e. *Mean date last pick*.—Averaging August 31$^{st}$
f. *Cluster density*.—Medium.
g. *Berries per cluster*.—8.6 berries per cluster.
h. *Unripe fruit color*.—Pantone color 15-0336 (Herbal Garden).
i. *Ripe berry color*.—Pantone color 16-3919 (Purple Cloud).
j. *Berry skin color after polishing*.—Pantone Color 19-4013 (Dark Navy).
k. *Berry surface wax abundance*.—High.
l. *Berry flesh color*.—Pantone color 13-0317 (Lilly Green).
m. *Berry weight*.—Average 2.510 g.
n. *Berry height from calyx to scar*.—11.778 mm.
o. *Berry diameter*.—18.100 mm.
p. *Calyx aperture*.—Average 7.817 mm.
q. *Calyx depth*.—Average 1.105 mm.
r. *Pedicel length*.—Average 8.932 mm.
s. *Pedicel surface texture*.—Smooth.
t. *Berry detachment force*.—Medium-hard.
u. *Berry shape*.—Oblate.
v. *Fruit stem scar*.—1.684 mm.
w. *Sweetness when ripe*.—Medium.
x. *Firmness when ripe*.—Firm.
y. *Acidity when ripe*.—Medium.
z. *Storage quality*.—Good at 42 days normal cold storage at +/−1C.

SEED

General:
a. *Seed abundance in fruit*.—Average.
b. *Seed color*.—Pantone color 17-1134 (Brown Sugar).
c. *Seed dry weight*.—0.267 mg. per seed.
d. *Seed length*.—Average 1.5 mm.

COMPARISON BETWEEN PARENTAL AND COMMERCIAL CULTIVARS

TABLE 1

| Denomination of similar variety | Characteristic for comparison | State of expression of similar variety | State of expression of candidate variety 'FC12-205' |
|---|---|---|---|
| 'Liberty' (U.S. Plant Patent No. 15,146) | Vigor | Low | High |
| 'Legacy' | Bloom retention | Medium | High |

TABLE 1-continued

| Denomination of similar variety | Characteristic for comparison | State of expression of similar variety | State of expression of candidate variety 'FC12-205' |
|---|---|---|---|
| 'Aurora' (U.S. Plant Patent No. 15,185) | Season | Very Late | Late |
| 'Aurora' (U.S. Plant Patent No. 15,185) | Acidity | High | Medium |

TABLE 1-continued

| Denomination of similar variety | Characteristic for comparison | State of expression of similar variety | State of expression of candidate variety 'FC12-205' |
|---|---|---|---|
| 'ZF06-264' | Fruit Size | Medium | Large |
| 'ZF06-103' | Growth habit | Semi-sprawl | Upright |

The invention claimed is:

1. A new and distinct variety of blueberry plant named 'FC12-205', substantially as illustrated and described herein.

* * * * *